United States Patent [19]

Sankey

[11] Patent Number: 5,449,772
[45] Date of Patent: Sep. 12, 1995

[54] CONTINUOUS PROCESS FOR THE PREPARATION OF SUCROSE 6-ESTERS

[75] Inventor: George H. Sankey, Reading, Great Britain

[73] Assignee: Tate & Lyle Public Ltd. Co., Great Britain

[21] Appl. No.: 64,852

[22] Filed: May 20, 1993

Related U.S. Application Data

[63] Continuation-in-part of Ser. No. 886,971, May 21, 1992, abandoned.

[30] Foreign Application Priority Data

May 21, 1991 [GB] United Kingdom ............... 9110821

[51] Int. Cl.$^6$ .................. G07H 13/02; G07H 1/00
[52] U.S. Cl. .................... 536/115; 536/116; 536/119; 536/120; 536/124
[58] Field of Search .......... 536/119, 120, 115, 124, 536/116

[56] References Cited

U.S. PATENT DOCUMENTS

| | | | |
|---|---|---|---|
| 4,557,927 | 12/1985 | Miyake et al. | 536/4.1 |
| 4,721,780 | 1/1988 | McDaniel, Jr. et al. | 536/120 |
| 4,889,928 | 12/1989 | Simpson | 536/115 |
| 4,996,306 | 2/1991 | McDaniel, Jr. et al. | 536/120 |
| 5,141,860 | 8/1992 | Bornemann et al. | 435/100 |

FOREIGN PATENT DOCUMENTS 0260979 3/1988 European Pat. Off. .

Primary Examiner—Michael G. Wityshyn
Assistant Examiner—Everett White
Attorney, Agent, or Firm—Ostrolenk, Faber, Gerb & Soffen

[57] ABSTRACT

A method is provided for the preparation of a sucrose 6-ester by: (i) reacting a solution of sucrose in an inert organic solvent with a reagent selected from the group consisting of a trialkyl orthoester and a ketene acetal, in the presence of an acid catalyst to provide a sucrose alkyl 4,6-orthoester, (ii) treating the sucrose alkyl 4,6-orthoester under mild aqueous acidic conditions to provide a mixture of sucrose 4- and 6-monoesters, (iii) treating the mixture of esters with a base to convert the sucrose 4-ester into sucrose 6-ester, and (iv) neutralizing the solution and isolating the sucrose 6-ester, in which stage (i) is effected in a continuous manner by passing the solution of sucrose and reagent through a strong acid macroreticular ion exchange resin at ambient temperature. Sucralose is prepared by chlorinating the sucrose 6-esters obtained.

18 Claims, No Drawings

CONTINUOUS PROCESS FOR THE PREPARATION OF SUCROSE 6-ESTERS

This invention is a continuation in part of U.S. application Ser. No. 07/886,971 filed May 21, 1992 now abandoned.

BACKGROUND OF THE INVENTION

This invention relates to an improved process for the preparation of sucrose 6-esters, which are key intermediates in one route to the production of sucralose (1,6-dichloro-,1,6-dideoxy-$\beta$-D-fructofuranosyl 4-chloro-4-deoxy-$\alpha$-D-galactopyranoside), which is disclosed in British Patent No. 1,543,167.

The preparation of sucralose involves the introduction of chlorine atoms into the 1'-and 6'- positions (i.e. displacement of two of the three primary hydroxyl groups) and at the 4-position (i.e. displacement of a secondary hydroxyl group). The third primary hydroxyl group, at the 6-position, must remain unaffected.

One important route to sucralose involves the preparation and subsequent chlorination of 2,3,6,3',4'-penta-O-acetyl sucrose in which the three hydroxyl groups to be displaced by chlorine atoms are unprotected while all the other hydroxyl groups are protected (see, for example, U.S. Pat. No. 4,362,869 and UK Patent GB 2 065 648 B).

An alternative, simpler route involves the preparation of a sucrose 6-ester which can be selectively chlorinated at the 4-, 1'- and 6'- positions and then de-esterified to provide sucralose. One such method of preparing sucrose 6-esters and converting them to sucralose is disclosed in UK Patent GB 2 079 749 B, but this method produces a mixture of acylated sucrose derivatives with substituents at one or more of the primary positions, with a major proportion of the 6-ester.

A more selective method of preparing sucrose 6-esters, disclosed in UK Patent GB 2 195 632 B, is based upon the preparation of a sucrose alkyl 4,6-orthoester by reacting sucrose with a trialkyl orthoacylate in the presence of an acid catalyst in an inert organic solvent, followed by hydrolysis of the orthoester to provide a mixture of sucrose 4- and 6-esters, which are then isomerized to provide a high yield of the required sucrose 6-ester. Ketene acetals, such as 1,1-dimethoxyethene, are useful alternatives to trialkyl orthoacylates in the preparation of sucrose alkyl 4,6-orthoesters, as disclosed in UK Patent Application 2255975A.

The method of GB 2 195 632 B is more efficient than that of GB 2 079 749 B, but involves several stages, each utilizing a different acid or base which must be removed.

I have now found that the method of GB 2 195 632 B can be operated by using acidic ion exchange resins to catalyze the preparation of the sucrose alkyl 4,6-orthoester and to hydrolyze it to a mixture of sucrose 4- and 6-esters, and then treating the hydrolyzate with a base to convert the sucrose 4-ester to sucrose 6-ester. The process can be run continuously to produce a mixture of sucrose 4- and 6-esters, without the need to add or remove acid.

Acidic ion exchange resins are reported to catalyze a variety of chemical reactions (Lazlo P (Ed.),1987, "Preparative chemistry using supported reagents", Academic Press, Inc., pp 209-211), but they have not been used to catalyze the preparation of sucrose derivatives. On the other hand, acidic ion exchangers have been used to effect various hydrolyses, including the inversion of sucrose (S Sussman, 1946, Industrial and Engineering Chemistry, 38,12,pp 1228-1230).

Robert L Albright (Reactive Polymers, 4, 1986, pp 155-174) reviews the use of porous polymers as supports for catalytic agents. He provides provisional guidelines for selecting a polymer for a given type of reaction while observing that not all the necessary knowledge is available to allow for an accurate selection.

Glycosidation of some monosaccharides are reported to be catalyzed by acidic ion exchange resins, including the preparation of methyl mannoside and methyl arabinoside (D F Mowery, 1961, J. Org. Chem., 26, pp 3484-3486) and propyl or butyl monoglucosides and propyl monoxyloside (U.S. Pat. Nos. 4,721,780 and No. 4,996,306).

Both of the above mentioned US patents mention that the process is applicable to water soluble di-, tri- and tetrasaccharide materials, but there is no enabling disclosure of such use. In view of the use of acidic ion exchangers to hydrolyze aqueous solutions of sucrose, the process might not be suitable for the production of disaccharide esters.

Acidic ion exchange resins have been used to catalyze reactions between ketones and orthoformates in discontinuous and continuous processes. Thus, S A Patwardhan and S Dev, 1974, Synthesis, pp 348-9, disclose a discontinuous method for the preparation of acetals using relatively large amounts of a macroreticular sulfonic acid resin (0.25 g per 1 g ketone) and triethyl orthoformate (5 molar equivalents per mole of ketone) under nitrogen at 0°–5° C.

European Patent Application No. 423745 discloses a continuous process for the preparation of 2,2-dimethoxy-3-methylbutane, in which a reaction mixture comprising approximately equimolar amounts of methyl isopropyl ketone, trimethyl orthoformate and methanol is flowed over an acid contact catalyst at 50°–70° C. Acid ion exchange resins taken from the wide range of those commercially available are used as the catalyst for the reaction of the ketone with the orthoformate and the methanol.

I have found that a continuous procedure of the type disclosed in EP-A-423745 can be applied to the preparation of sucrose alkyl 4,6-orthoesters by flowing the reactants over an acid ion exchanger, provided that: (i) the acid ion exchanger is a strong acid macroreticular resin i.e. has a pKa<1 e.g. a sulfonic acid resin; (ii) the reactants are dissolved in an inert organic solvent, such as dimethyl formamide, which does not take part in the reaction; and (iii) the reaction takes place at ambient temperature.

The reaction between sucrose and the trialkyl orthoacylate or ketene acetal is effected by passing a solution of the reactants in an inert organic solvent through a strong acid macroreticular resin, which acts as the catalyst without causing degradation of the sucrose. Weak acid macroreticular resins (pKa>1) do not catalyze the reaction and strong acid non-porous resins (pKa<1) are much less effective than their macroreticular counterparts.

Thus, according to the present invention, there is provided a method for the preparation of a sucrose 6-ester by: (i) reacting a solution of sucrose in an inert organic solvent with a reagent selected from the group consisting of a trialkyl orthoester and a ketene acetal, in the presence of an acid catalyst, to provide a sucrose alkyl 4,6-orthoester, (ii) treating the sucrose alkyl 4,6-orthoester under mild aqueous acidic conditions to provide a mixture of sucrose 4- and 6-monoesters, (iii) treating the mixture of esters with a base to convert the sucrose 4-ester into sucrose 6-ester, and (iv) neutralizing the solution and isolating the sucrose 6-ester, in which stage (i) is effected in a continuous manner by passing the solution of sucrose and reagent through a strong acid macroreticular ion exchange resin at ambient temperature.

The inert organic solvent for the reaction mixture is preferably an N,N-dialkylacetamide or an N,N-dialkylformamide, such as dimethyl formamide, although pyridine is also of interest.

Stages (i) and (ii) of the process can be run continuously by passing a solution of sucrose and the reagent in an inert organic solvent such as dimethylformamide through a column of macroreticular acid resin, continuously adding water to the eluate containing the sucrose alkyl 4,6-orthoester, and passing the aqueous solution through a second column of acidic ion exchange resin to effect the hydrolysis.

I have found that Amberlyst 15(H+) macroreticular resin is suitable for the first stage and that it is convenient to use the same resin for stage (ii).

In general, the amount of trialkyl orthoester or ketene acetal used in step (i) can vary from about 1 to 2 ME per ME of sucrose, preferably from 1.1 to 1.5 ME.

Conversion of the sucrose 4-ester to sucrose 6-ester can be carried out by adding a water soluble base such as potassium carbonate or sodium carbonate. Alternatively, an organic base such as tertiary butylamine can be used.

Use of a readily water soluble base such as potassium carbonate lends itself to continuous operation more easily than a less soluble base such as calcium hydroxide. Thus, the eluate from stage (ii) can be collected in a holding tank, into which the base is metered to provide the appropriate concentration for migration of the ester group from the 4- to the 6- position.

The base must be neutralized before concentration and isolation of the sucrose 6-ester, in order to prevent degradation of the product. Neutralization can be effected by addition of a suitable acid or, preferably, by passage through an acidic ion exchange resin to give a stream free from inorganic salts.

The sucrose 6-ester can be isolated by concentrating the neutralized solution to a syrup, dissolving the syrup in methanol, seeding, and collecting the crystalline product. After washing, e.g. with methanol, and drying, the sucrose 6-ester can be stored until required.

Sucrose 6-esters prepared according to the present invention can be used as intermediates for the production of sucralose. Thus, in a further embodiment of the present invention there is provided a process for the production of sucralose, by preparing a sucrose 6-ester, reacting the sucrose 6-ester with a chlorinating agent capable of selectively chlorinating the 4-, 1'- and 6'- positions, optionally peresterifying the sucralose 6-ester so formed, de-esterifying the sucralose ester, and recovering sucralose, in which the sucrose 6-ester is prepared by:

(i) passing a solution of sucrose and a trialkyl orthoester or a ketene acetal in an inert organic solvent through a strong acid macroreticular resin at ambient temperature to provide an eluate containing a sucrose alkyl 4,6-orthoester;

(ii) continuously adding water to the eluate and passing the mixture through an acidic ion exchange resin to hydrolyze the sucrose alkyl 4,6-orthoester and to provide an eluate containing a mixture of sucrose 4- and 6- monoesters;

(iii) treating the mixture of esters with a base to convert the sucrose 4-ester to sucrose 6-ester, and (iv) neutralizing the solution and isolating the sucrose 6-ester.

DESCRIPTION OF THE PREFERRED EMBODIMENTS

The invention is further illustrated by the following Examples.

EXAMPLE 1

Tests with Three Different Acid Ion Exchange Resins for the Preparation of Sucrose Methyl 4,6-Orthoacetate A solution of sucrose (300 g) and trimethyl orthoacetate (135 ml; 1.2 ME) in dimethylformamide (1500 ml) was made up and cooled to 25° C. Portions of this solution were passed down columns of three different ion exchange resins at ambient temperature at a rate of 10 g/minute and the effluent was collected and analyzed by thin layer chromatography (n-BuOH/EtOH/$H_2O$, 5:3:2). The results are summarized as follows:

| Resin (H+) | Acidity | Porosity | Activity: initial | after 30 min |
|---|---|---|---|---|
| Amberlyst 15 | strong (pKa <1) | high* | very good | very good |
| Amberlite IR-120 | strong (pKa <1) | nil | fair | nil |
| Amberlite IRC-50 | weak (pKa 5.7) | high* | nil | nil |

*macroreticular

EXAMPLE 2

Preparation of Sucrose 6-Acetate

A solution of sucrose (500 g) and trimethyl orthoacetate (225 ml; 1.2 ME) in dimethylformamide (2500 ml) was passed down a column of Amberlyst 15(H+) resin (25 g) at ambient temperature at a rate of 10 g/minute. Water was added continuously to the eluate issuing from the base of the column at a rate of 0.065 g water/g eluate and the diluted eluate was passed through a heat exchanger to cool the temperature from about 40° (heat of dilution) to about 25°. The cooled solution from the heat exchanger was then passed down a second column of Amberlyst 15(H+) resin (25 g) at a rate of 10.65 g/minute (i.e. at a rate which allowed the two columns to be run continuously in sequence).

A sample of the eluate from the second column (1851 g; equivalent to an input of 300 g of sucrose) was removed and treated with an aqueous 2% w/v solution of potassium carbonate ($K_2CO_3$. 1.5 $H_2O$; 37 ml). After one hour, the solution was neutralized with dilute hydrochloric acid (0.5 molar; 16.2 ml) and then concentrated to a syrup (451.2 g) under reduced pressure at 50°. Analysis of the syrup showed a yield of crude sucrose 6-acetate of about 75% with sucrose (about 15%) as the main impurity.

The syrup was dissolved in hot methanol (600 ml), allowed to cool to 40° and then seeded with crystalline sucrose 6-acetate (1.5 g). Crystallization was allowed to proceed overnight at ambient temperature and then the product was collected, washed with methanol (300 ml) and dried in vacuo at 40°. Yield 219.4 g; 50% molar; analysis: sucrose 6-acetate 82.8%, sucrose 4-acetate 0.5%, sucrose 4.7%, sucrose di-acetate 2.4%, methanol of crystallization 7%.

Similar results are obtained using 1,1-dimethoxyethene (150 ml) in place of the trimethyl orthoacetate.

I claim:

1. In the method for the preparation of a sucrose 6-ester by: (i) reacting a solution of sucrose in an inert organic solvent with a reagent selected from the group consisting of a trialkyl orthoester and a ketene acetal, in the presence of an acid catalyst, to provide a sucrose alkyl 4,6-orthoester, (ii) treating the sucrose alkyl 4,6-orthoester under mild aqueous acidic conditions to provide a mixture of sucrose 4- and 6-monoesters, (iii) treating the mixture of esters with a base to convert the sucrose 4-ester into sucrose 6-ester, and (iv) neutralizing the solution and isolating the sucrose 6-ester, the improvement in which step (i) is effected in a continuous manner by passing the solution of sucrose and said reagent through a strong acid macroreticular ion exchange resin of pKa<1 at ambient temperature.

2. The method of claim 1, in which the strong acidic ion exchange resin is Amberlyst 15 (H+3).

3. The method of claim 1, in which the amount of trialkyl orthoester or ketene acetal used in step (i) is from about 1 to 2 mole equivalents (ME) per ME of sucrose.

4. The method of claim 1, in which the amount of trialkyl orthoester or ketene acetal used in step (i) is from about 1.1 to 1.5 ME per ME of sucrose.

5. The method of claim 1, in which the base used to convert the sucrose 4-ester into the sucrose 6-ester is selected from the group consisting of water soluble bases and organic bases.

6. The method of claim 1, in which the base is neutralized after conversion of the sucrose 4-ester into the sucrose 6-ester by passing the basic solution through an acidic ion exchange resin.

7. The method of claim 1, in which a solution of sucrose and a trialkyl orthoester or a ketene acetal in an inert organic solvent is passed through a column of strong acid macroreticular resin to provide an eluate containing a sucrose alkyl 4,6-orthoester, water being continuously added to the eluate before passing the aqueous solution through a second column of acidic ion exchange resin to provide a mixture of sucrose 4- and 6-monoesters.

8. The method of claim 7, in which the amount of trialkyl orthoester or ketene acetal used is from about 1 to 2 ME per ME of sucrose.

9. The method of claim 7, in which the amount of trialkyl orthoester or ketene acetal used is from about 1.1 to 1.5 ME per ME of sucrose.

10. The method of claim 7, in which the base used to convert the sucrose 4-ester into the sucrose 6-ester is selected from the group consisting of water soluble bases and organic bases.

11. The method of claim 7, in which the mixture of sucrose 4- and 6- monoesters produced in step (ii) is collected in a holding tank into which is metered a water soluble base to effect conversion of the sucrose 4-ester into the sucrose 6-ester.

12. The method of claim 7, in which the base is neutralized after conversion of the sucrose 4-ester into the sucrose 6-ester by passing the basic solution through an acidic ion exchange resin.

13. In the method for the production of sucralose, comprising preparing a sucrose 6-ester, reacting the sucrose 6-ester with a chlorinating agent capable of selectively chlorinating the 4-, 1'- and 6' positions, optionally peresterifying the sucralose 6-ester so formed, de-esterifying the sucralose ester, and recovering sucralose, the improvement in which the sucrose 6-ester is prepared by:

(i) passing a solution of sucrose and a trialkyl orthoester or a ketene acetal in an inert organic solvent through a strong acid macroreticular resin to provide an eluate containing a sucrose alkyl 4,6-orthoester, (ii) continuously adding water to the eluate and passing the mixture through an acidic ion exchange resin to hydrolyze the sucrose alkyl 4,6-orthoester and to provide an eluate containing a mixture of sucrose 4- and 6- monoesters, (iii) treating the mixture of monoester with a base to convert the sucrose 4-monoester to sucrose 6-monoester, and (iv) neutralizing the solution and isolating the sucrose 6-monoester.

14. The method of claim 13, in which the amount of trialkyl orthoester or ketene acetal used is from about 1 to 2 ME per ME of sucrose.

15. The method of claim 13, in which the amount of trialkyl orthoester or ketene acetal used is from about 1.1 to 1.5 ME per ME of sucrose.

16. The method of claim 13, in which the base used to convert the sucrose 4-ester into the sucrose 6-ester is selected from the group consisting of water soluble bases and organic bases.

17. The method of claim 13, in which the mixture of sucrose 4- and 6- monoesters produced in step (ii) is collected in a holding tank into which is metered a water soluble base to effect conversion of the sucrose 4-monoester into the sucrose 6-monoester.

18. The method of claim 13, in which the base is neutralized after conversion of the sucrose 4-monoester into the sucrose 6-monoester by passing the basic solution through an acidic ion exchange resin.

* * * * *